United States Patent [19]

Staab et al.

[11] 4,220,415
[45] Sep. 2, 1980

[54] CONSTRUCTION FOR PHOTOMETRIC ANALYZER

[75] Inventors: Joachim Staab; Willy Apel, both of Frankfurt; Heinz Wolf, Kronberg, all of Fed. Rep. of Germany

[73] Assignee: Hartmann & Braun Aktiengesellschaft, Frankfurt am Main, Fed. Rep. of Germany

[21] Appl. No.: 955,095

[22] Filed: Oct. 26, 1978

[30] Foreign Application Priority Data

Nov. 5, 1977 [DE] Fed. Rep. of Germany ....... 2749662

[51] Int. Cl.³ .............................................. G01N 21/01
[52] U.S. Cl. .................................... 356/433; 250/343; 356/246
[58] Field of Search ......................... 356/246, 432–442; 250/243; 285/31; 403/294, 353; 248/264, 265, 298, DIG. 6

[56] References Cited
U.S. PATENT DOCUMENTS 3,672,632  6/1972  Chow .................................... 285/31
3,992,095  11/1976  Jacoby et al. ......................... 356/32

FOREIGN PATENT DOCUMENTS 1598535  11/1972  Fed. Rep. of Germany .

Primary Examiner—John K. Corbin
Assistant Examiner—Bruce Y. Arnold
Attorney, Agent, or Firm—Smyth, Pavitt, Siegemund, Jones & Martella

[57] ABSTRACT

An analyzer such as a two beam infrared analyzer is assembled in building block fashion and includes a radiation source module and a detection module tied together by rods and in optical alignment with each other. Intermediate or "cell"-modules are hung on the rods and all adjacent, interfacing faces of the several modules are constructed for indexing, preventing lateral deflection when the fastened rods hold all parts together.

4 Claims, 4 Drawing Figures

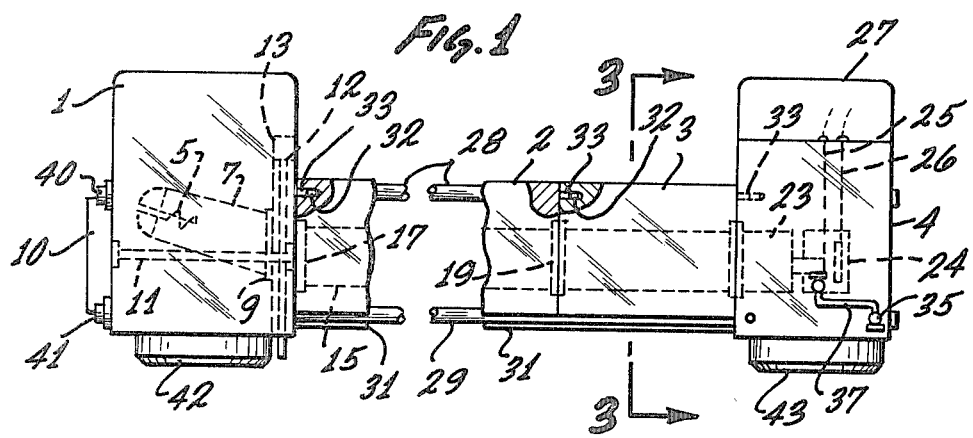

CONSTRUCTION FOR PHOTOMETRIC ANALYZER

BACKGROUND OF THE INVENTION

The present invention relates to a photometric analyzer constructed from several units or modules which are optically aligned.

A building block type or modular infrared gas analyzer is, for example, described in German Pat. No. 1,598,535. The analyzer is of overall cylindrical configuration and is composed of cylindrical modules. A first unit or module 2a includes radiation sources (23, 24), and a motor driven chopper 29. Second and third units or modules, 2b and 2c, include gas cells, such as for sample gas, filters, etc. Another unit or module 2d includes radiation detector cells and electrical circuit components for the immediate processing of detector signals. The entire assembly is mounted on a rail or bed 4, shown in FIG. 3 of that patent. Thus, the several units are only indirectly interconnected in that they are all connected to a common support.

DESCRIPTION OF THE INVENTION

It is an object of the present invention to provide a new and improved construction for radiation type analyzers which permits easy assembly of such analyzers from various building blocks.

In accordance with the preferred embodiment of the present invention, it is suggested to provide a radiation unit or module which contains the requisite source or sources for radiation, a modulating chopper, and an exit window or windows; preferably an interface is provided with indexing bores and/or pins; a second, radiation receiving unit or module contains one or more absorption cells and electrical transducer means for converting absorbed radiation into an electrical signal; preferably, this unit is also provided with an interface having such indexing means. Each of the two units or modules includes a pair of transverse bores, respectively, receiving rods, there being two rods each inserted in a bore of the radiation unit and in a bore of the detection unit; these rods are fastened to the units which, in turn, however, are spaced apart. One or more intermediate units or modules are interposed in optical alignment with the radiation and detection units, in that they are hung on these rods; they are preferably also provided with indexing means in appropriate interfaces so that in the entire assembly any two adjacent units are indexed to each other. The entire assembly is, therefore, self-supporting and the units are interconnected directly in the manner described. As long as optical interfacing so permits, any number and variety of units can be so assembled, the radiation and detection modules being, so to speak, respective end units tied together by the rods onto which one hangs any intermediate unit as is required for a particular measuring task.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a side view of a first example of the preferred embodiment of the invention, illustrating a two beam infrared analyzer;

FIG. 2 is a top view of the device shown in FIG. 1;

FIG. 3 is a sectional view taken along line 3—3 in FIG. 1, but showing how one unit is being interposed; and FIG. 4 is a section view through a modified intermediate unit.

Proceeding now to the detailed description of the drawings, the figures show a radiation unit or module 1, intermediate gas cell units or modules 2 and 3, and a detection and receiving unit or module 4. The radiation unit is provided as a metal parallelepiped which contains a pair of diverging ducts 6 and 7 joined in a chamber which contains a source 5 of infrared radiation. The other ends of the ducts 6, 7 are closed by means of windows, 8 and 9, which permit radiation to pass.

The module 1 includes additionally a modulator which is comprised of a disk 12 or diaphragm, having apertures to permit the passage of radiation, alternating with inhibition on account of rotation of the disk. The disk 12 is contained in a shallow recess 13 of block 1, the latter being also provided with a bore containing a shaft 11 which is the drive shaft of the disk or diaphragm 12. A motor 10 is affixed to the rear of block or module 1, and shaft 11 is the output shaft of the motor. Upon rotation of the shaft, the radiation exiting through windows 8 and 9 is periodically interrupted by the disk 12.

The second unit or module in line is a cell module 2 being also constructed as a metal block of parallelepiped configuration, but having smaller transverse dimension in one direction than unit 1. The module 2 contains two cylindrical bores 14 and 15, defining the cells and being closed by means of radiation transparent windows 16 and 18 for bore and cell 14, and 17 and 19 for bore and cell 25. The entrance windows 16 and 17 are, respectively, aligned with the exit windows 8 and 9 of unit 1.

The cell 14 is additionally provided with entrance and/or exit nipples 20 and 21 for passing sample gas through the cell, for example, on a continuous basis. The cell 15 may contain a reference gas or, preferably, a gas which does not absorb the radiation, at least not within the band of interest. Alternatively, the two cells 14 and 15 may be fluid conductively interconnected, or still alternatively, cell 15 may have also nipples for any suitable or desirable gas connection.

A second cell unit or module 3 is constructed similarly to unit 2. It has two bores closed by radiation transmissive windows and being provided for optical alignment with the cells 14, 15 of unit 2. The unit 3 is actually an optional feature of the device as a whole, and its cells may be provided for purposes of enhancing selectivity. For example, the cells of that unit contain gas having, for example particular filtering properties. This unit could be omitted or replaced by a unit which contains merely solid state filters, such as interference type filters, etc.; of course, one does not need additional windows in this case.

The receiver unit or module 4 is again constructed as a metal block which, for example, contains two detection chambers 22, 23, filled with gas of the type to be detected in the sample gas which flows through cell 14. A differential pressure chamber 24 is included in unit 4; the chamber 24 is divided by a membrane or flexible diaphragm, and opposite chamber sides are connected, respectively, to the two chambers 22 and 23. The diaphragm is one electrode of a capacitor which capacitor changes its capacitance upon flexing of the membrane. Thus, the differential pressure is converted into an electrical signal (transducing). The pressure differential changes with the concentration of the measuring gas in the sample gas.

Reference numerals 25 and 26 refer to the leads by means of which the capacitor is connected to an amplifier which is contained in a case 27, which, in turn, is stuck onto the unit 4.

The two end modules 1 and 4 each have two bores, traversing each of the blocks and provided to receive two rods 28 and 29. The rods 28 and 29 have on one end each several transverse bores 38 and 39, respectively, and the unit 4 is provided with two transverse bores, each can be aligned with one of the bores (38, 39) of the respectively inserted rod. Pins 34 and 35 are mounted to block 4 by means of pivot linkages 36, 37, and these pins can be inserted into the bores 38, 39, respectively, to hold the rods 28, 29 in unit 4, and fastening the rods on that one end in this particular fashion. The other ends of rods 28, 29 are provided with threaded bores, and screws 40 and 41, and are respectively threaded into the rods and tightened against the block 1.

It will readily be understood that the interposed units 2 and 3 serve also as spacers for this mode of fastening of the modules 1 and 4 to each other. The different transverse slots 38 and 39 in rods 28, 29 are provided to accommodate the unit to differently long "spacer" units 2 and 3. It will also be appreciated that one can use other types of nut fastenings on the ends of the rods, and threaded fasteners generally could be provided on both ends each. Also, the pin and threaded fastenings as shown could be reversed by having pins lock the rods to unit 1 and having a threaded fastening provided on unit 4.

The units 2 and 3, as stated, are interposed between units 1 and 4. Moreover, these intermediate units are provided with longitudinal grooves or notches 30 and 31 in and along approximately diametrical edges. These notches are contoured, so that the units 2 and 3 can be suspended by and onto rods 28, 29. One side of each unit 2, 3 and 4 is provided with two index bores 32. The sides of units 1, 2 and 3, will, respectively, face these first mentioned sides in the assembled device and are provided with index pins 33. Conveniently, one may provide each interfacing end face of the several units with one indexing bore and one indexing pin. It is essential that faces of the several units are transversely oriented to any optical path in the system, that they interface with another unit, and are indexed in the desired lateral position.

It can thus be seen that the device and system can very simply be assembled. The rods 28 and 29 are simply inserted into the appropriate bores of the end units 1 and 4, leaving more space between them than in the final assembly. Next, the units 2 and 3 are hung onto rods 28, 29 by first inserting rod 28 into the respective grooves or notches 30 and swinging the units in so that grooves or notches 31 engage rod 29. Thereafter units 2 and 3 are shifted towards unit 4 and towards each other, so that the indexing pins 32 enter indexing bores 33. Unit 1 is shifted against unit 2 in the same fashion of indexing. The rods 28 and 29 are next shifted so that one of their bores 38 each is aligned with bores in unit 4 into which pins 34 and 35 will be inserted to hold the rods 28, 29. Finally, nut fasteners or screws 40, 41 are threaded into threaded ends of the rods to tighten the units together.

FIG. 4 illustrates a modification in the construction of any of the intermediate units 2 and 3. In this case, each unit is provided with just two end plates such as 46 containing the requisite windows and being provided with notches 30, 31. The chambers are established in this case by tubes 44 and 45. A unit constructed in that manner can be assembled with the remainder of the system just as described, as the notches 30, 31 provide for the requisite suspension. The tubes plus end plates function also as spacers, the end plates 41 being additionally provided with indexing bores and pins. Intermediate units of the type 2 and 3, as well as of the type of FIG. 4, can be used interchangeably.

It can readily be seen that the invention provides for a compact, self-supporting infrared gas analyzer being of modular design whereby different module constructions can be used in different assemblies. The units 2 and 3 can be of different lengths and supplemented or replaced by other modules whose main construction requirement is to permit suspension on the rods and indexing alignment with other adjacent units or modules to obtain the requisite optical alignment. The principle expounded is applicable to single beam construction or other assemblies for different measuring tasks.

Typical infrared measuring systems that can be realized by the invention (as far as construction is concerned) are disclosed as to analysis features in U.S. Pat. Nos. 3,970,387; 3,937,962; 3,925,667; 3,740,555; 3,725,702 and possibly others. In each instance, one has a radiation unit, a detection unit and intermediate units containing cells for gas. Each of these units may well be differently constructed, e.g. for single or dual sources of radiation, or constituting a more complex detection chamber assembly; or containing differently constructed cell units which permit pneumatic interconnection, etc. A plurality of modules constructed for physical alignment in an assembly as described can be assembled in building block fashion to accommodate a large variety of different tasks.

The invention is not limited to the embodiments described above but all changes and modifications thereof not constituting departures from the spirit and scope of the invention are intended to be included.

We claim:

1. Photometric analyzer construction, comprising:
   a first unit of block construction containing at least one source of radiation, at least one radiation duct with an exit adjacent to or in said face and a movable modulating diaphragm, said block having additionally two parallel, traversing bores;
   a second unit of block construction containing at least one radiation absorption detector and means for converting absorbed radiation into an electrical signal, the second unit also having two parallel bores;
   a pair of rods, respectively, inserted into one bore each of sad first and second units and optically aligning them with regard to emitted and detected radiation;
   means for fastening the rods to the units to, thereby, interconnect them; and
   at least one intermediate unit containing at least one gas cell and having notches for being suspended by the rods as extending between the first and second units, thereby spacing the first and second units, said fastening means holding the units together in abutting relationship.

2. Construction as in claim 1, one of the first and second units being provided with transverse bores, said rods each having also at least one transverse bore adjacent one of their ends, the fastening means include pins, respectively, traversing the transverse bores to hold the rods in the longitudinal bores, the fastening means including threaded fastening means at the other ends of the rods for fastening them to the other one of the first and second units.

3. Construction as in claim 1 or 2, wherein said units are provided with planar interfaces for abutment of respective adjacent ones of the units, there being indexing pins and indexing bores, respectively, in interfacing faces of adjacent units.

4. Construction as in claim 1, at least one of the units constructed as blocks, containing bores optically aligned with a bore or bores in an adjacent unit or units.

* * * * *